(12) United States Patent
Wood

(10) Patent No.: US 6,515,492 B1
(45) Date of Patent: Feb. 4, 2003

(54) PARTICLE DETECTOR SYSTEM

(75) Inventor: Michael Anthony Wood, Leamington Spa (GB)

(73) Assignee: Microbial Systems Limited (GB)

( * ) Notice: Subject to any disclaimer, the term of this patent is extended or adjusted under 35 U.S.C. 154(b) by 0 days.

(21) Appl. No.: 09/700,346

(22) PCT Filed: May 17, 1999

(86) PCT No.: PCT/GB99/01558

§ 371 (c)(1),
(2), (4) Date: Jan. 11, 2001

(87) PCT Pub. No.: WO99/60378

PCT Pub. Date: Nov. 25, 1999

(30) Foreign Application Priority Data

May 16, 1998 (GB) .............................. 9810493

(51) Int. Cl.[7] .............................................. G01R 27/08
(52) U.S. Cl. ....................................... 324/702; 324/71.4
(58) Field of Search ........................ 73/865.5; 324/609, 324/702, 71.4; 356/72, 73, 410; 359/298

(56) References Cited

U.S. PATENT DOCUMENTS

| | | | | |
|---|---|---|---|---|
| 4,198,160 A | * | 4/1980 | Kachel et al. ................. | 356/72 |
| 4,341,993 A | * | 7/1982 | Brunsting et al. ............. | 377/10 |
| 4,673,288 A | | 6/1987 | Thomas et al. ................ | 356/72 |
| 4,790,653 A | | 12/1988 | North, Jr. ..................... | 356/73 |
| 4,818,103 A | | 4/1989 | Thomas et al. ................ | 356/72 |
| 4,850,001 A | * | 7/1989 | Duysings et al. .............. | 378/54 |
| 4,997,275 A | * | 3/1991 | Gaucher et al. ............... | 356/72 |
| 5,106,187 A | * | 4/1992 | Bezanson ..................... | 356/73 |
| 5,616,501 A | | 4/1997 | Rodriguez et al. ............. | 436/63 |
| 6,288,783 B1 | * | 9/2001 | Auad ........................... | 356/410 |
| 6,389,912 B1 | * | 5/2002 | Wood ........................... | 73/865.5 |

FOREIGN PATENT DOCUMENTS

| | | |
|---|---|---|
| EP | 0 279 000 A1 | 8/1988 |
| EP | 0 780 679 A2 | 6/1997 |
| GB | 2 319 618 A | 5/1998 |
| WO | WO 90/12308 | 10/1990 |

* cited by examiner

*Primary Examiner*—N. Le
*Assistant Examiner*—Walter Benson
(74) *Attorney, Agent, or Firm*—Woodcock Washburn LLP

(57) ABSTRACT

A combined impedance and fluorescence particle detecting system comprising a divider separating a first and a second chamber, the divider having a small orifice enabling flow of liquid sample between the chambers, and technique for determining an impedance signal representative of variations in impedance at the orifice due to the flow therethrough of particles within the liquid sample; a light source for irradiating the particles within the orifice and a detector for receiving a fluorescence signal emitted by the particles within the orifice, such that the impedance signal and fluorescence signal are substantially synchronous and wherein the divider comprises a plate through which the orifice passes, the plate being disposed within the system such that the direction of measurement of impedance and the incident direction of light at the orifice are both substantially perpendicular to the plane of the plate.

22 Claims, 7 Drawing Sheets

PARTICLE DETECTOR SYSTEM

The invention relates to a particle detector which combines the techniques of electrical impedance measurements and fluorescence from particles.

It is known to detect particles such as blood cells or yeast cells for example within a sample by passing the particle through a narrow orifice and detecting variations in the impedance across the orifice. Additionally, it is known to dye or stain samples with a suitable fluorescent dye and then illuminate the particles with a suitable light source such as a laser beam having a fundamental frequency, and thereafter determine the state of the particles by the fluorescence signal emitted from the particles.

However, such known systems are very complex, costly, require continuous adjustment and are limited in terms of minimum size of particles that can be detected. An object of the invention is to improve particle size and fluorescence particle detection systems. In particular, the invention seeks to enable use of a relatively narrow diameter orifice to provide accurate particle size measurements down to a small size whilst at the same time allowing fluorescence detection and preferably enabling detection and/or clearance of any blockages which might occur at the orifice.

According to one aspect of the invention there is provided a combined impedance and fluorescence particle detecting system comprising;

a plate separating a first and second chamber, the plate having a small orifice, preferably less than 150 microns in diameter, enabling the flow of particles between the chambers, and means for determining variations in impedance at the orifice due to the flow of particles therethrough;

a light source for irradiating the particles within or close to the orifice and a detector for receiving light emitted by the particles; and Preferably means for clearing the orifice without removal of the plate from the system, and/or means for detecting orifice blockages is also provided. Other preferred features are set out in the attached claims and following description.

An embodiment of the invention will now be described, by way of example only, with reference to the accompanying drawings, in which FIG. 1 is a schematic perspective view of part of the system according to invention;

Figure 1:
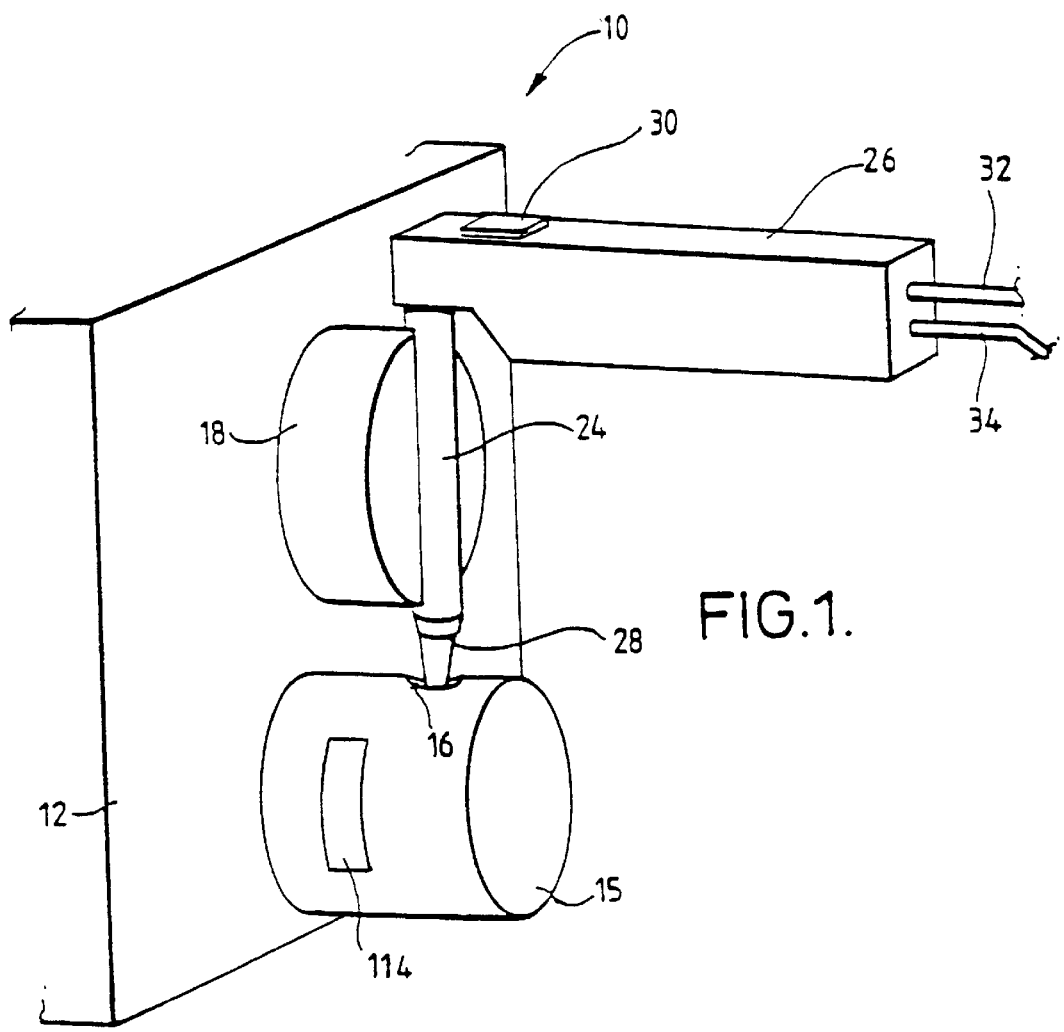
Figure 2:
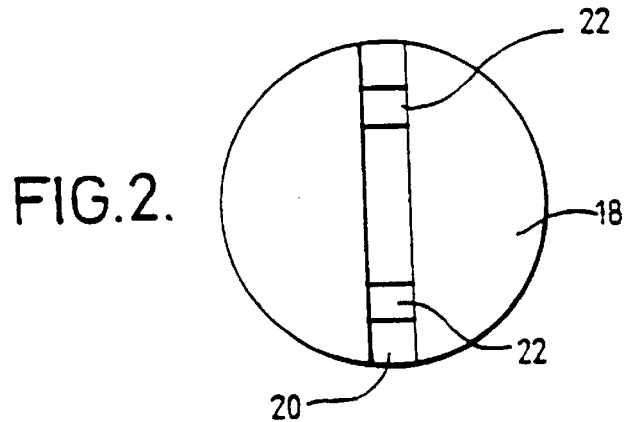
FIG. 2 is a schematic front elevation view of the sample alignment guide show FIG. 1.
Figure 4:
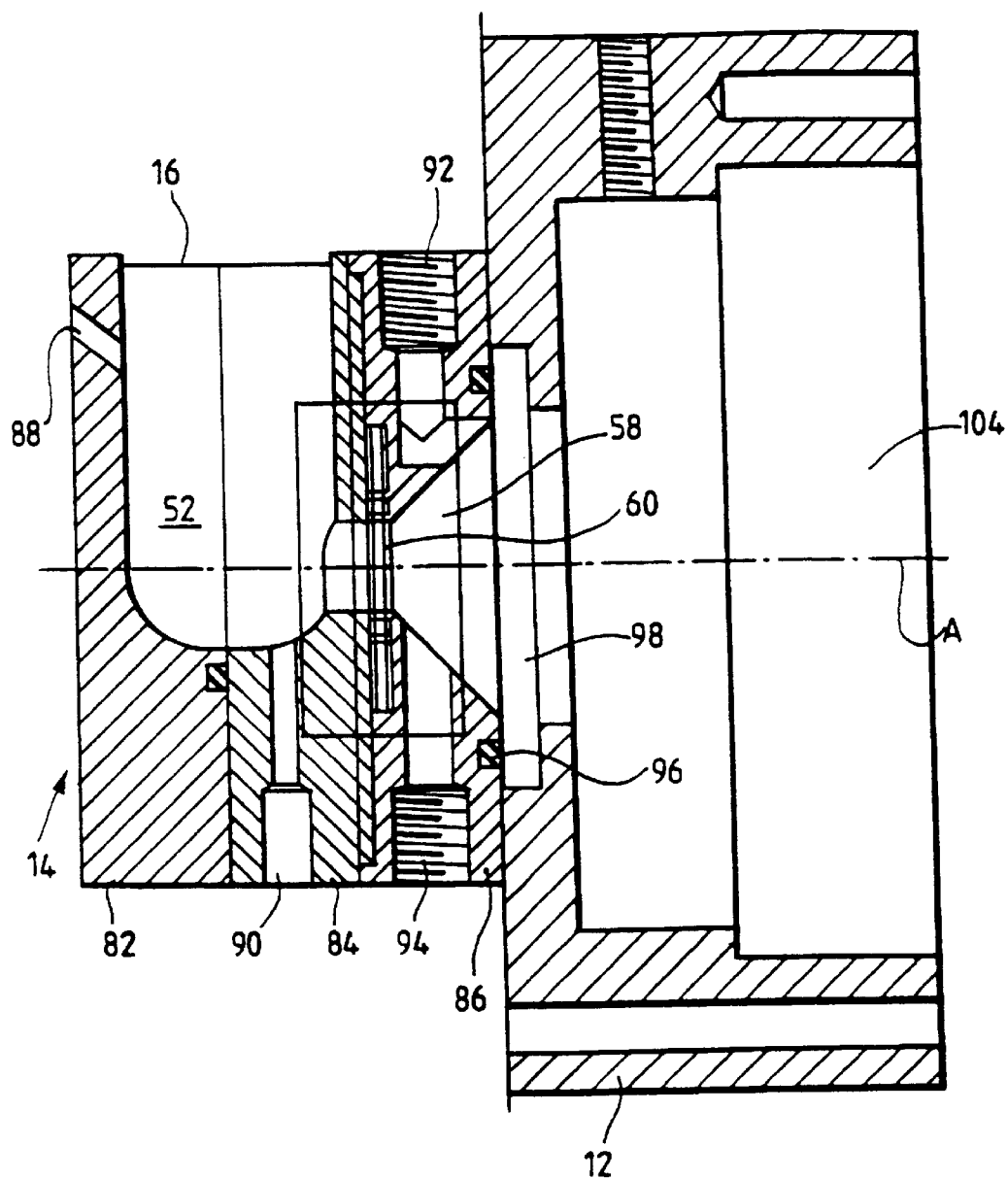
FIG. 4 is a schematic cross sectional side elevation view of the sample chamber according to the invention and part of the main housing for a laser.

Referring to FIG. 1 there is shown part of a combined impedance and fluorescence particle detecting apparatus 10 according to the invention comprising a main housing 12 from which protrudes a sample chamber housing 14 enclosed in a shield 15 having an inlet 16 through which a sample passes into a first chamber 52 shown in FIG. 4. Shield 15 and housing 14 comprising an aperture for receiving a light detector 114 described later which may preferably be a photo-multiplier. Additionally, a wand guide 18 protrudes from housing 12. Wand guide 18 comprises a vertical groove 20 which enables alignment of nozzle 24 of handheld wand 26 with inlet 16. Hand-held wand 26 further comprises a replaceable tip 28, a button 30, a fluid inlet pipe 32 and electrical connection 34. As shown in FIG. 2, wand guide 18 comprises a pair of detectors 22 such as optical detectors to determine if wand nozzle 24 is in place within groove 20.

Figure 3:
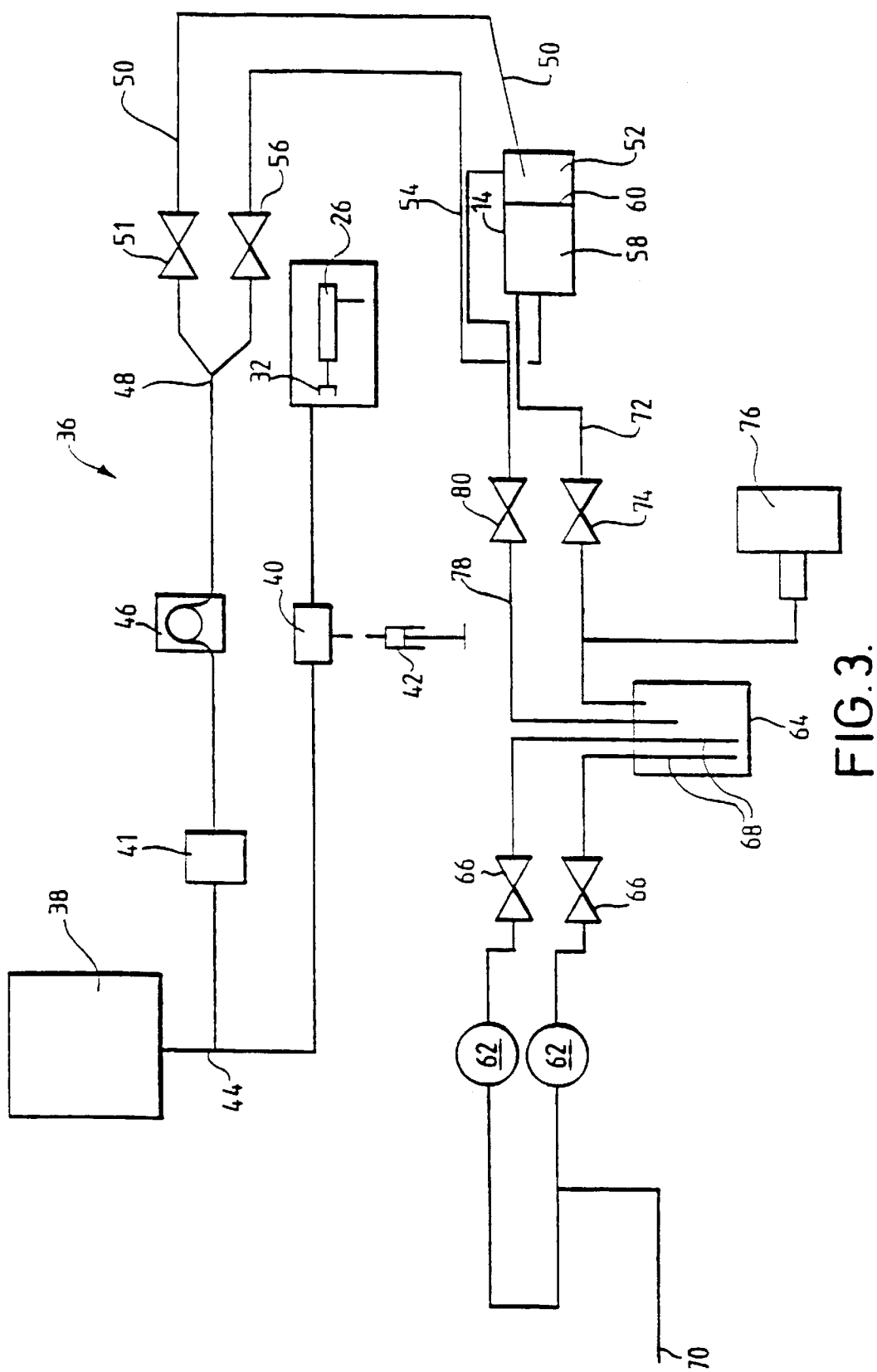
FIG. 3 is a schematic block diagram of the fluid control circuit according to invention.

Referring to FIG. 3 there is shown a schematic drawing of the fluid control system 36 used in apparatus 10. In fluid control system 36 a diluent reservoir 38, which can house say three liters of electrolyte for example, is connected along one path to a three-way valve 40 which is connected at one outlet to a syringe drive 42 which can comprise a 12 volt stepper motor for example, and at another outlet is connectable to wand 26 by fluid inlet pipe 32.

Reservoir 38 is also connected via a T-connector 44 to a diluent sensor 41, which can be an optical device for determining if diluent is present. A pump 46 such as a 12 volt DC peristaltic pump, drives diluent to sample chamber housing 14 via a Y-connector 48.

One outlet of Y-connector 48 is connected to tube 50 having a valve 51 such as an electrically operated pinch valve, which controls flow of diluent through tube 50 to a first chamber 52 forming part of a sample chamber housing 14. The other outlet from Y-connector 48 passes through tube 54 which has a valve 56, again such as an electrically driven pinch valve, which controls flow of fluid through tube 54 into a second chamber 58 of the sample chamber housing 14. First and second chambers 52 and 58 respectively, are separated by a divider and flow restrictor 60 having an orifice 63 (see FIGS. 6,7,8 and 9). Sample chamber 14 is shown in greater detail in FIGS. 4 and 5.

Fluid control system 36 further comprises a suction system comprising a pair of vacuum pumps 62. Each pump is connected to a vacuum reservoir 64 via a valve 66, such as an electrically driven pinch valve. Purge tubes 68 pass almost to the bottom of reservoir 64 thereby to enable expulsion of any liquid in reservoir 64 via at least one of valves 66, pump 62 and outlet 70 thus for disposal.

Reservoir 64 is farther connected via tube 72 to the second chamber 58 of housing 14. Tube 72 Ether comprises a valve 74 such as a pinch valve and pressure transducer 76 such as a Honeywell Controls type 141PCO5G device. Reservoir 64 is further connected to the first sample chamber 52 via tube 78 having a valve 80.

Referring to FIGS. 1 and 4 to 9, sample chamber housing 14 preferably comprises an outer shield 15 (made of conductive material) to shield against electromagnetic radiation. Inlet 16 leads to first chamber 52 which is separated from second chamber 58 by flow restrictor, plate, or divider 60. The chambers can be made in a body of inert material such as an acrylic or other plastic.

In this embodiment, first chamber 52 is formed using a first part 82 and second part 84 which can be attached for example using threaded screws and threaded apertures and sealed to prevent leakage for example using a suitable gasket or membrane. First part 82 (as shown in FIG. 4) comprises a liquid inlet 88 which is inclined so as to direct incoming diluent from tube 50 towards chamber divider 60. Second part 84 comprises a fluid outlet 90 (connectable to tube 78) enabling drainage of first chamber 52. First part 84 further comprises a narrowing towards divider 60, and also a bore (not shown) enabling an electrode to be located within chamber 52.

Figure 5:
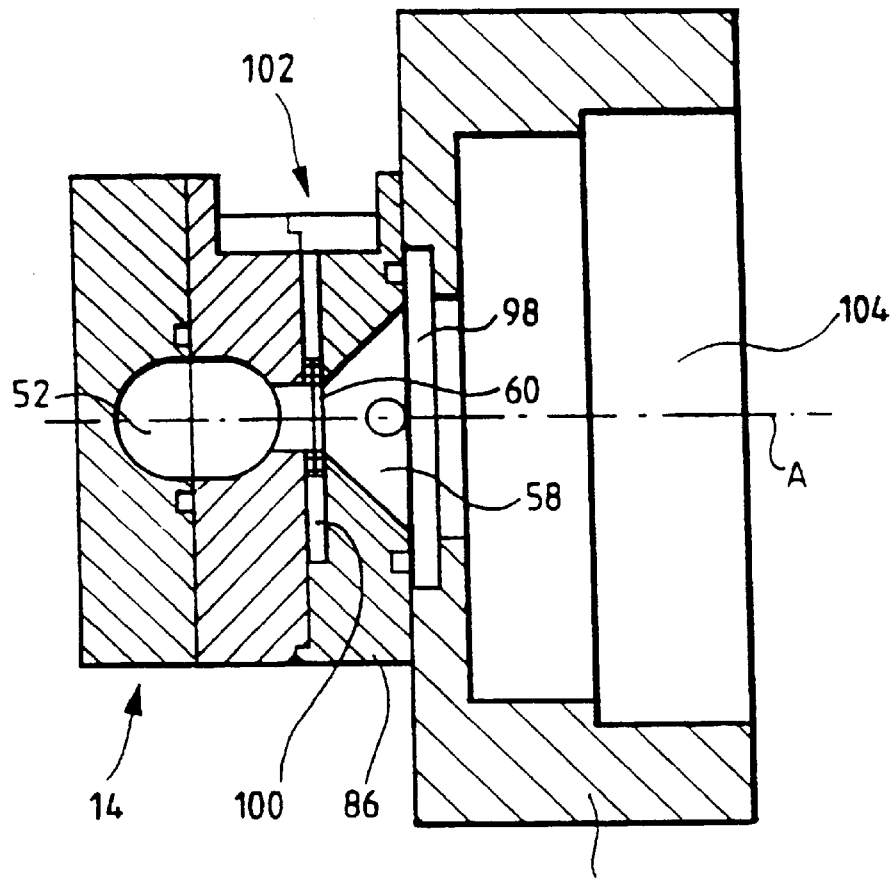
FIG. 5 is a schematic cross sectional plan view of the sample chamber show FIG. 4.

Chamber housing 14 comprises a third part 86 which defines in part, second chamber 58. Third part 86 comprises a liquid inlet 92 and outlet 94 for inlet and drainage of diluent into the second chamber 58. Additionally, as best seen in FIG. 5, third part 86 is attached to main housing 12 again for example using threaded screws and threaded receiving apertures not shown, so as to align housing 14, and in particular aperture 63, with an axis A. Accordingly, third part 86 abuts a transparent plate 98 which can for example be made of glass and which is in particular free of defects in the region about axis A. Third part 86 comprises an annular recess 96 for an O-ring which abuts plate 98 to seal the abutment against fluid egress from chamber 58. A chamber 104 is defined in main housing 12 for receiving a laser (not shown) which directs laser light towards divider 60 along axis A.

Referring to FIG. 5, it can be seen that third part 86 defines a slot 100 for receiving divider 60 and also an outer recess 102 for receiving a light filter and detector 114 as described later.

Figure 6:
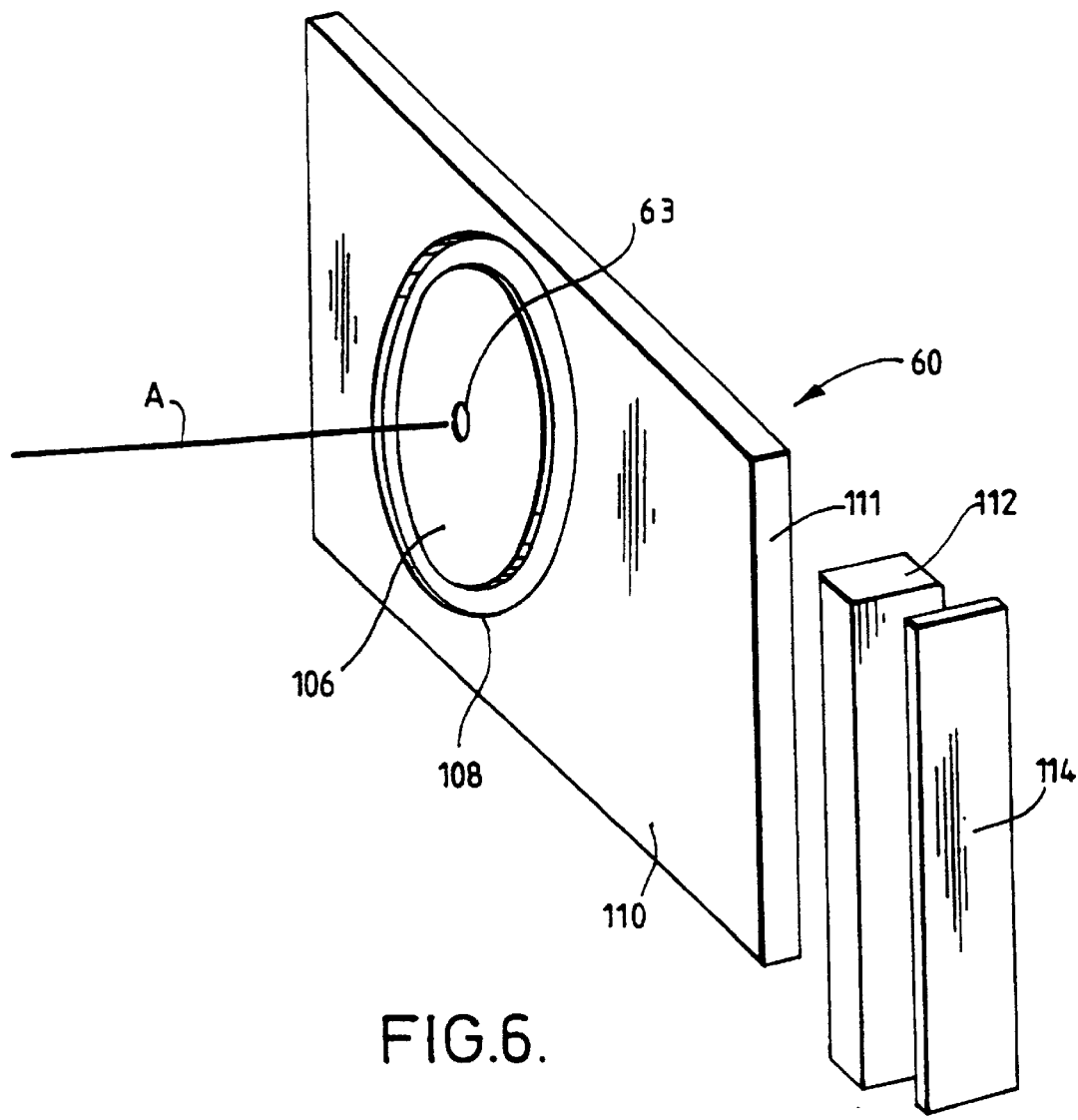
FIG. 6 is a schematic exploded perspective view of a chamber divider and orifice according to the invention.
Figure 7:
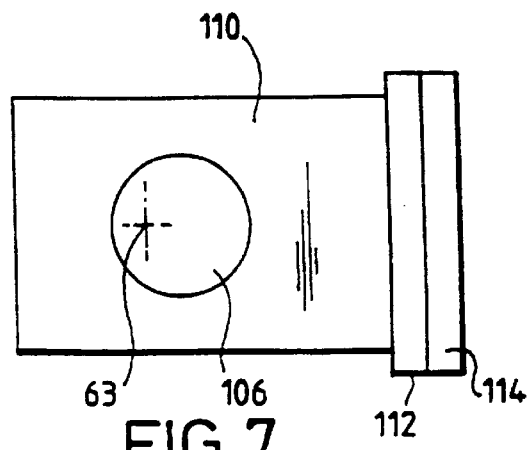
FIGS. 7 and 8 are front elevation view and end view of the divider shown in FIG. 6.
Figure 8:
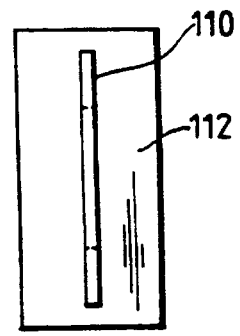

The divider 60 which provides the particle flow restrictor is shown in greater details in FIGS. 6 to 8. In particular, the restrictor comprises a disc 106 which defines the orifice 63 which is aligned with axis A. The disc 106 is preferably made from crystalline material such as ruby or sapphire and in particular material which exhibits a piezo electric effect. The disc 106 is mounted in an aperture 108 in plate 110 for example using a suitable refractive adhesive or cement. Plate 110 can for example be a glass slide which is transmissive at the desired frequency and enables transmission of light internally through to an end edge 111 which abuts a filter 112 which in turn abuts a light detector 114, such as a photo-multiplier.

As shown in FIG. 7, the orifice 63 can be displaced from the centre of disc 106 for example to place it at a focal point of internal reflections within disc 106. A non-central focal point can be achieved for example if the surfaces of the disc 106 are treated to increase internal reflections, for example by silvering, as well as an edge of disc 106 about orifice 63. The surfaces and edges (except edge 111) of plate 110 can also be treated to increase internal reflections and thereby increase transmission of light through to filter 112 and detector 114.

Figure 9:
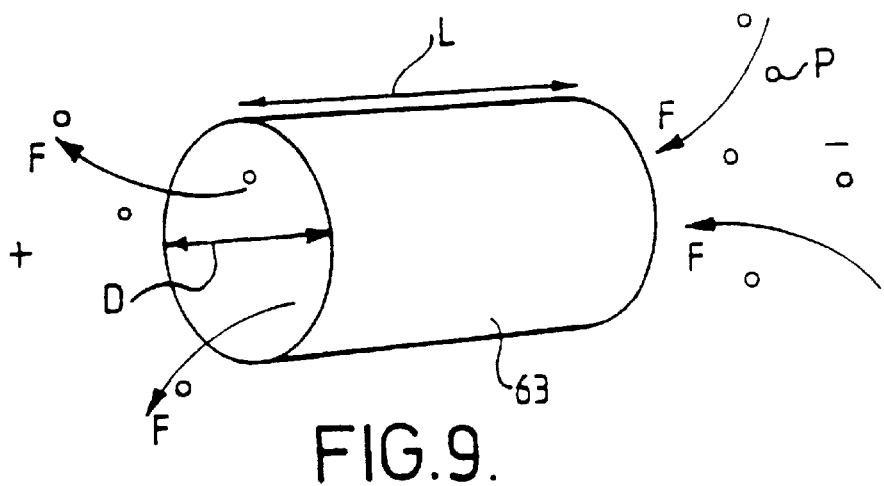
FIG 9 is a schematic perspective view of the orifice.

As shown in FIG. 9 orifice 63 has length L and diameter D, for example a length of 80 microns and diameter of 30 microns is preferred for certain sizes or volumes of particle P which during measurement flow through orifice 63 along direction F. However, other sizes of orifice are possible, in particular about 50 to 60 microns and preferably less than 150 microns.

Figure 10:
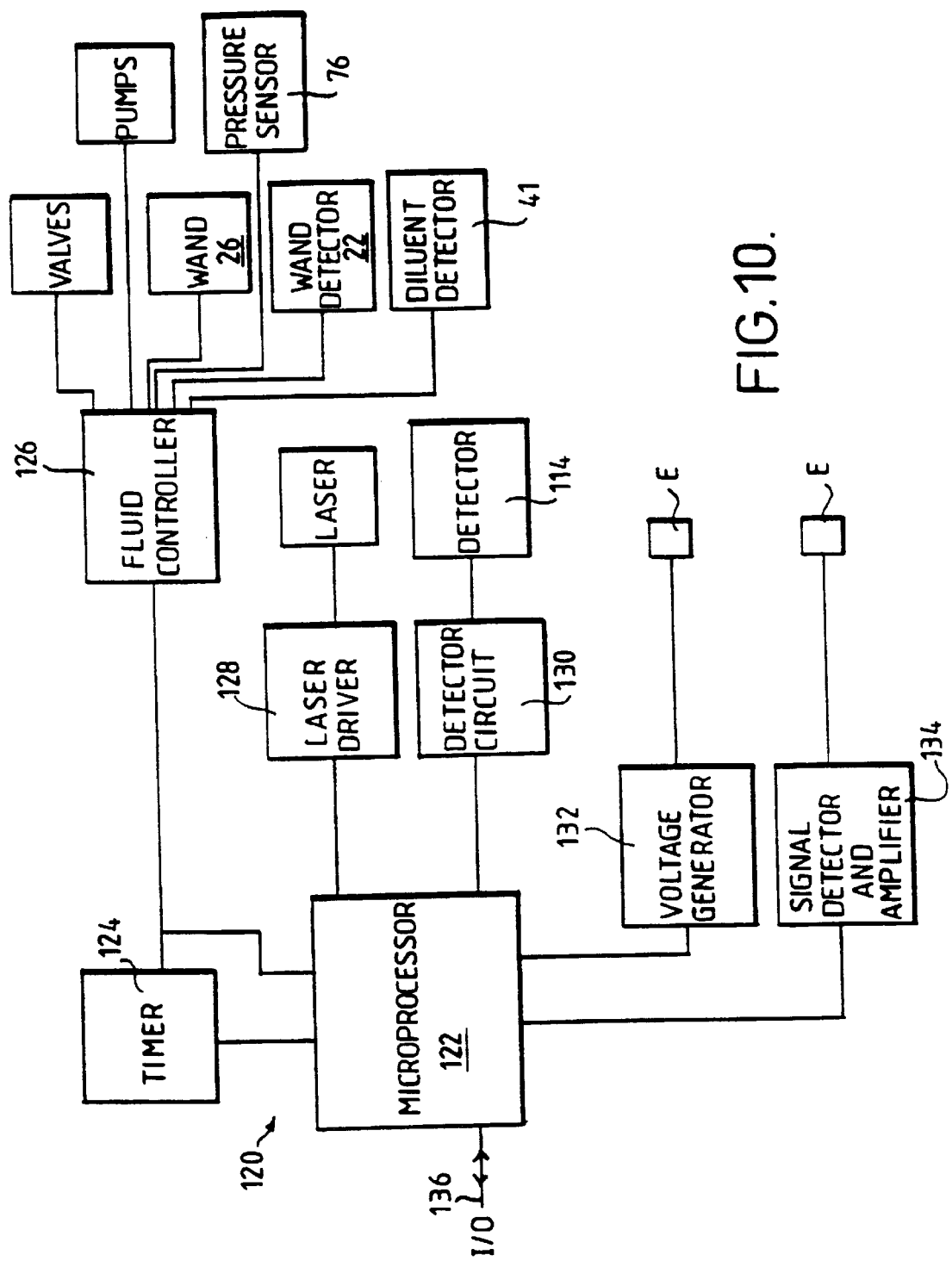
FIG. 10 is a schematic block diagram of the electronic control system according to the invention.

Referring to FIG. 10 there is shown a schematic block diagram of a suitable electronics control system 120 for particle detection system 10. The control system 120 comprises a microprocessor 122 having a timer 124 and at least one input output port 136 for external communications. Additionally, the system 120 comprises a fluid controller 126 (which in reality may be formed at least in part by microprocessor 122) which controller actuates the valves 40. 51. 56, 66, 74 and 80 of the fluid control system shown in FIG. 3 as described earlier. Furthermore, communication with controller 126 enables controller wand 26 to actuate pumps 42, due to actuation of the on/off button 30. Controller 126 further operably communicates with pumps 46 and 62, the diluent detector 31, wand detector 22 and pressure sensor 76. Microprocessor 122 operably communicates with controller 126 thereby to control the operation of the physical integers of the fluid control system 36.

Figure 11:
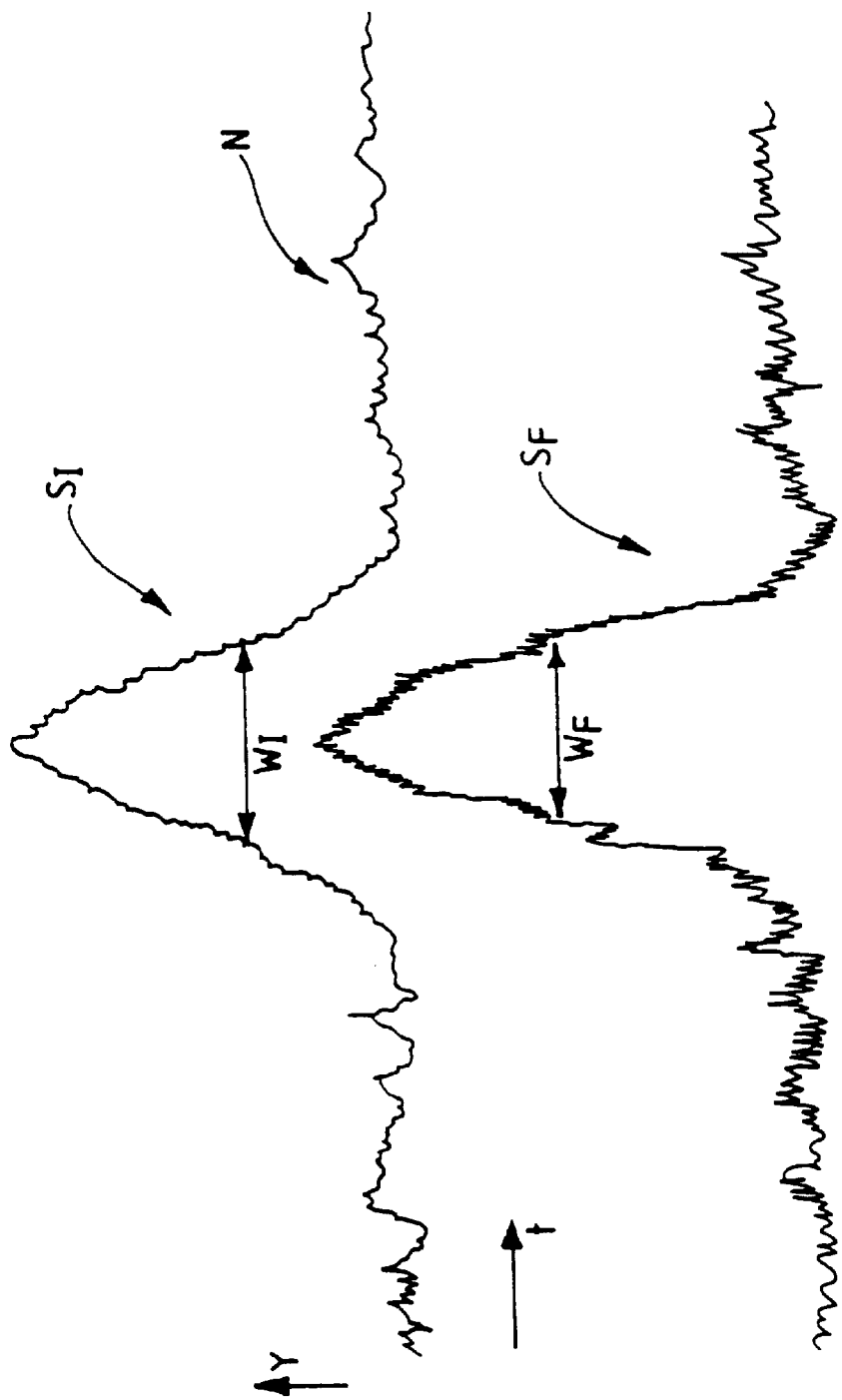
FIG. 11 is a schematic drawing of typical impedance and fluorescence signals detected by the system.

System 120 further comprises a laser driver 128 and fluorescence detection circuit 130, for example comprising detector chip 114, for detection of signal SF shown FIG. 11. The driver 128 and detector 130 are both operably in communication with microprocessor 122.

System 120 further comprises a pulse generator 132 for providing an electrical output signal to an electrode E positioned within one of chambers 52 or 58. An impedance signal detector and amplifier 134 is operably in communication with a second electrode in the other one of chambers 52 or 58 which amplifier 134 is also in communication with microprocessor 122 to enable analysis of a signal S shown by way of example in FIG. 11.

As can be seen from FIG. 11 a typical impedance signal $S_1$ comprises a peak having a width W at half maximum whereby the signal $S_1$ is distinguishable from background noise N. Similarly fluorescence signal 54 has a width at half maximum of $W_1$.

In use, a user takes wand 26 and inserts a clean nozzle 28 into a sample. By pressing button 30, fluid controller 126 actuates drive 42 and valve 40 so as to effect a measured suction of sample into nozzle 28. Wand 26 is then placed in guide 18. When sensors 22 have communicated detection of nozzle 24 therein, controller 126 actuates drive 42 and valve 40 so as to expel the gathered sample into first chamber 52 via inlet 16. A desired volume of diluent from reservoir 38 can also be presented to chamber 52 via wand 26 again using drive 42 or alternatively through inlet 88 using pump 46. Chamber 58 is filled with the electrolytic diluent from chamber 38 using pump 46 which passes diluent trough tube 54 via inlet 92 into chamber 58. Accordingly, an electrical path can be provided between electrodes E via orifice 63 to enable detection of particles flowing through orifice 63 using detection of variation in the impedance between the electrodes as detected at detector and amplifier 134. The impedance detection can be facilitated by applying a DC voltage of about 20-40 V across electrodes E and for example generator 132 can be configured to drive a constant current between the electrodes. An AC voltage can also be used.

To increase flow of particles between first chamber 52 and second chamber 58, a pressure differential is created between the chambers using vacuum reservoir 64. Fluid controller 126 ensures that the pressure on line 72 is sufficiently low to encourage a certain flow of particles through orifice 63 which are of course pushed through under the pressure differential into chamber 58 and out through tube 72 via valve 74 (which is of course open to reservoir 64). Several evacuations of reservoir 64 using pumps 62 and valves 66 may be required during a period of measurement of say 30 seconds on a given sample.

At the beginning of the measurement period, pulse generator 132 applies an initial calibration signal which is detected by detector 134 and which can be analyzed by microprocessor 122 against a preset standard. A series of pulses, of say up to 1 volt at say 10 kz can be applied to one of the electrodes by generator 132.

If the calibration pulses are acceptable compared to the present standard measurement can begin. Otherwise recalibration can follow. Repeated failure can lead eventually to cleaning procedures being commenced.

The voltage at second electrode is measured by detector 134 and transmitted to microprocessor 122 for example for batch analysis of data collected over say a 32 millisecond duration.

Simultaneously and/or alternatively, a laser beam is directed along axis A towards orifice 63 which irradiates particles passing through the orifice 63. By suitably dying or staining the particles in the sample with a known fluorescent dye, the particles emit a fluorescent signal (shifted away to a lower frequency or higher wavelength than the incident radiation). This light is emitted in random directions. However, by irradiating the particles at orifice 63 much of the emitted light passes into disc 106 where it is internally reflected by the disc 106 and slide 110. The light then passes through edge 111 and subsequently filter 112 into detector chip 114. The laser is driven by driver 128 and the detected light from detector chip 114 passes through to detector circuit 130 for analysis by microprocessor 122.

As can be seen from FIG. 11 the impedance signal $S_I$ and $S_F$ are substantially synchronous using this technique. Two channels of data for the same period, say 32 ms, can be transferred to microprocessor 122 for analysis of both the impedance and fluorescence signals.

Between fluorescence and/or impedance measurements. It is possible to clear orifice 63 by applying a suitable pulse sequence across electrodes E. For example, a high frequency burst of in order of 10 kHz and a DC voltage of about 1 volt can be applied for example for a period of three batches of one second with half second intervals.

There are several possibilities for clearing the orifice 63 including application of electrical pulses (such bursts of 10 kHz 1V signals such as the calibration signal), flow reversal, removal of the constant current or high tension voltage, removal of the sample from chamber 52 and subsequent cleaning for example by directing diluent through inlet 88 at orifice 63. Flow reversal can be achieved by allowing diluent to pass into chamber 58 whilst closing off valve 74 and drawing sample away from chamber 52 through outlet 90, i.e. by opening valve 80 which is connected to tube 78 and vacuum reservoir 64. Preferably reversal process is tried first before reverting to removal of the sample from chamber 52. However, each technique can be used independently, or in combination with the others.

This clearance technique can be applied uniformly throughout the measurement period on a given sample. Alternatively, impedance signal detector 134 or fluorescent detector 130 can be used to detect a blockage due to analysis by microprocessor 122 of the detected results of the impedance and/or fluorescence measurements. A total blockage or partial blockage can be determined by microprocessor 122 in any one of the following ways.

(a) The incidence of a single or average rate of incidence of detected fluorescence and/or impedance signals $S_p$ and $S_I$ falls below a predetermined rate;

(b) The intensity of detected fluorescence and/or impedance signals $S_F$ and $S_I$ falls below a predetermined value;

(c) The width of a fluorescence and/or an impedance signal $S_F$ and $S_i$ is above a predetermined size;

(d) The average width of a number of impedance signals S is above a predetermined size;

(e) The voltage of the mean base line or noise base line of the impedance measurements varies above a predetermined value from the initial base line voltage or other determined value;

(f) The height of a fluorescence and/or an impedance signal $S_F$ and $S_I$ exceeds a predetermined value;

(g) The fluorescence and/or electrical background noise varies in a predetermined way such as having certain amplitude variation within a predetermined frequency range; and/or (h) The current between electrodes E varies in a predetermined way or above or below a predetermined value or percentage such as 5 or 10%.

In the unlikely event that such a blockage is unable to be cleared using the application of high frequency pulses, it may be necessary to drain sample chambers 52 and 58 and wash the plate 60 on line by injecting diluent into chamber 52 especially directed at divider 60 through inlet jet 88. Repeated pulses of diluent directed at divider 60 and suction of diluent out of chamber 58 using vacuum reservoir 64 whilst having inlet 92 closed (i.e. at valve 56) clears apertures 63. If this is not the case, the divider 60 can of course be removed for manual cleaning.

After cleaning, or after sample removal by draining chamber 62 and 58 using outlets 90 and 94 respectively, the chambers 52 and 58 can be cleaned by repeated filling and evacuation using diluent from reservoir 38. Accordingly, when first chamber 52 is again empty, a new sample can be introduced as described earlier.

What is claimed is:

1. A combined impedance and fluorescence particle detecting system comprising a divider separating a first and a second chamber, the divider having a small orifice enabling flow of liquid sample between the chambers, and means for determining an impedance signal representative of variations in impedance at the orifice due to the flow therethrough of particles within the liquid sample; a light source for irradiating the particles within the orifice and a detector for receiving a fluorescence signal emitted by the particles within the orifice, such that the impedance signal and the fluorescence signal are substantially synchronous and wherein the divider comprises a plate through which the orifice passes, the plate being disposed within the system such that the direction of measurement of impedance and the incident direction of light at the orifice are both substantially perpendicular to the plane of the plate.

2. The system according to claim 1 wherein the incident direction of light at the orifice is substantially opposite to the direction of flow of particles at the orifice.

3. The system according to claim 1 comprising a chamber housing for the first and the second chamber.

4. The system according to claim 3 having a main housing for system components, and wherein the chamber housing is detachably mountable on part of the main housing through which part light is operably emitted from the light source.

5. The system according to claim 3 wherein the sample chamber comprises a slot for receiving the divider which slot enables insertion and removal of the divider from its operative position.

6. The system according to claim 5 wherein the chamber housing and divider are configured to ensure that on insertion of the divider into the slots, the orifice is aligned with the incident radiation from the light source.

7. The system according to claim 3 wherein the chamber housing comprises at least a two part construction enabling separation of the two parts for example for ease of cleaning.

8. The system according to claim 7 wherein the first chamber is defined by separable first and second parts.

9. The system according to claim 3 wherein the second chamber comprises an inlet aperture for incident light from the light source and means for preventing ingress or egress of fluid through the aperture in use.

10. The system according to claim 1 comprising means for clearing the orifice without removal of the divider from the system.

11. The system according to claim 10 wherein the clearing means comprises a voltage generator which enables the application of a burst of electrical pulses across the orifice.

12. The system according to claim 11 wherein the voltage of the pulses is in the order of one volt, and preferably the pulse frequency is in the order of 10 kHz.

13. The system according to claim 11 wherein the voltage generator applies a constant current across the orifice as the clearing means effects removal of the voltage across the orifice in order to assist in the clearing thereof.

14. The system according to claim 12 wherein the frequency of the electrical pulses is in the order of 10 kHz.

15. The system according to claim 1 wherein the first chamber comprises an inlet for sample and/or diluent, and an outlet.

16. The system according to claim 15 wherein a clearing means selectively inputs diluent through the inlet of the first or second chamber and/or removes diluent or sample through the outlets from the first or second chambers.

17. The system according to claim 1 wherein the second chamber comprises an inlet for diluent and/or sample, and an outlet.

18. The system according to claim 1 wherein the diameter of the orifice is less than 150 microns, and more preferably less than 60 microns.

19. The system according to claim 18 wherein the orifice diameter is in the order of 30 microns.

20. The system according to claim 18 wherein the diameter of the surface is less than 60 microns.

21. The system according to claim 1 comprising an orifice blockage detector.

22. The system according to claim 21 wherein the blockage detector determines one or more of:

the incidence of a single or average rate of incidence of detected fluorescence and/or impedance signals to determine if the rate falls below a predetermined rate, if the intensity of detected fluorescence and/or impedance signals falls below a predetermined value, if the width of a fluorescence and/or impedance signal is above a predetermined size, if the average width of a number of fluorescence and/or impedance signals is above a predetermined size, if the voltage of the mean base line or noise base line of the impedance measurements where is above a predetermined value from the initial voltage and/or other determined value, if the height of a fluorescence and/or impedance signal exceeds a predetermined value, if the fluorescence and/or electrical background noise varies in a predetermined way such as having certain amplitude variations with any predetermined frequency range, and/or if the current between the electrodes varies in a predetermined way such as above or below a predetermined value or percentage such as 5 or 10%.

* * * * *